United States Patent
Hamamoto et al.

(10) Patent No.: US 10,543,275 B2
(45) Date of Patent: *Jan. 28, 2020

(54) COMPOSITION FOR PATCH PREPARATION COMPRISING DRUG, ORGANIC SOLVENT, LIPOPHILIC MASS BASE, AND POWDER

(71) Applicant: MEDRX CO., LTD., Kagawa (JP)

(72) Inventors: Hidetoshi Hamamoto, Kagawa (JP); Katsuhiro Yamanaka, Kagawa (JP); Takahiro Tanimoto, Kagawa (JP)

(73) Assignee: MEDRX CO., LTD., Kagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/408,649

(22) PCT Filed: Jun. 18, 2013

(86) PCT No.: PCT/JP2013/066765
§ 371 (c)(1),
(2) Date: Dec. 17, 2014

(87) PCT Pub. No.: WO2013/191187
PCT Pub. Date: Dec. 27, 2013

(65) Prior Publication Data
US 2015/0174249 A1    Jun. 25, 2015

(30) Foreign Application Priority Data
Jun. 20, 2012 (JP) ................. 2012-139215

(51) Int. Cl.
| | | |
|---|---|---|
| *A61K 47/18* | (2017.01) | |
| *A61K 31/7088* | (2006.01) | |
| *A61K 9/70* | (2006.01) | |
| *A61K 31/165* | (2006.01) | |
| *A61K 31/167* | (2006.01) | |
| *A61K 31/407* | (2006.01) | |
| *A61K 31/485* | (2006.01) | |
| *A61K 38/23* | (2006.01) | |
| *A61K 47/32* | (2006.01) | |
| *A61K 47/38* | (2006.01) | |
| *A61K 47/14* | (2017.01) | |

(52) U.S. Cl.
CPC ........... *A61K 47/18* (2013.01); *A61K 9/7053* (2013.01); *A61K 31/165* (2013.01); *A61K 31/167* (2013.01); *A61K 31/407* (2013.01); *A61K 31/485* (2013.01); *A61K 31/7088* (2013.01); *A61K 38/23* (2013.01); *A61K 47/14* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 5,811,117 A | 9/1998 | Hashimoto et al. | |
| 6,503,532 B1 | 1/2003 | Murty et al. | |
| 7,785,622 B2 * | 8/2010 | Ito | A61K 9/7053 424/449 |
| 2004/0086552 A1 | 5/2004 | Klokkers et al. | |
| 2006/0036220 A1 * | 2/2006 | Kawahara | A61K 9/0048 604/294 |
| 2009/0258063 A1 * | 10/2009 | Udagawa | A61K 9/7061 424/449 |
| 2009/0317452 A1 | 12/2009 | Komoda et al. | |
| 2011/0189261 A1 | 8/2011 | Kuribayashi et al. | |
| 2012/0065599 A1 * | 3/2012 | Eifler | A61K 9/7061 604/290 |

FOREIGN PATENT DOCUMENTS

| | | |
|---|---|---|
| JP | H06-016542 A | 1/1994 |
| JP | H06-145050 A | 5/1994 |
| JP | H07-145047 A | 6/1995 |
| JP | H08-027003 A | 1/1996 |
| JP | H09-136834 A | 5/1997 |
| JP | H09-169636 A | 6/1997 |
| JP | 2004-502725 A | 1/2004 |
| JP | 2011-74035 A | 4/2011 |
| WO | 2008/032719 A1 | 3/2008 |
| WO | 2009/066457 A1 | 5/2009 |
| WO | 2009/110351 A1 | 9/2009 |
| WO | 2010/113225 A1 | 10/2010 |

OTHER PUBLICATIONS

Office Action issued in corresponding Australian Patent Application No. 2013278403 dated Mar. 29, 2017.
English Translation of Submission of Publication dated Jan. 23, 2017 submitted in corresponding Japanese Patent Application No. 2014-521482.
English Translation of Office Action dated Mar. 21, 2017 issuing from corresponding Japanese Patent Application No. 2014-521482.
Office Action issued in corresponding Japanese Patent Application No. 2014-521482 dated Dec. 19, 2017.
International Search Report issued in corresponding International Patent Application No. PCT/JP2013/066765 dated Jul. 16, 2013.
Extended European Search Report issued in corresponding European Patent Application No. 13806076.9 dated Oct. 20, 2015.

\* cited by examiner

*Primary Examiner* — David J Blanchard
*Assistant Examiner* — Daniel F. Coughlin
(74) *Attorney, Agent, or Firm* — Morgan, Lewis & Bockius LLP

(57) ABSTRACT

The present disclosure provides a composition for a non-aqueous patch preparation with excellent adhesibility which can sustainedly release a drug. The patch preparation can improve the adhesibility of the patch preparation and the release property of a drug by the addition of a powder ingredient the long-time sustention of the adhesibility of tape preparations enables an improvement of the transdermal absorbability and the sustained release of a drug.

21 Claims, 1 Drawing Sheet

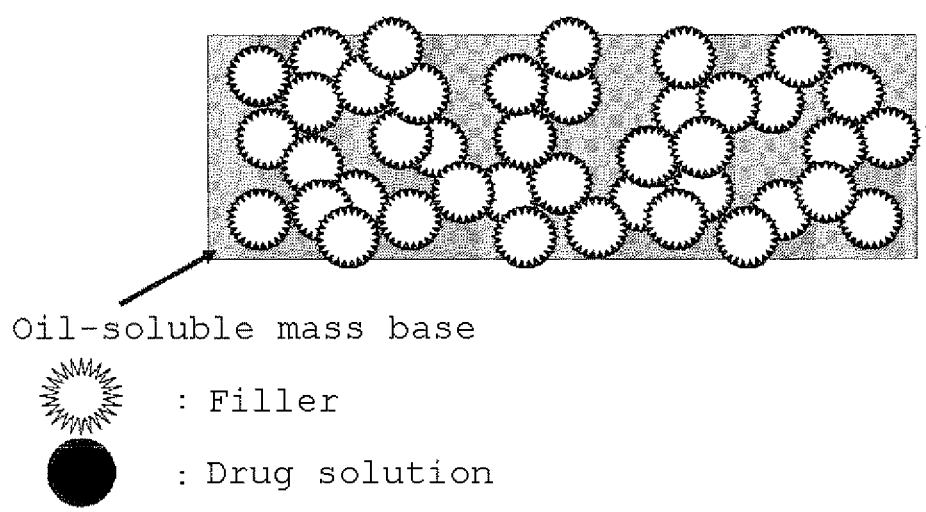

COMPOSITION FOR PATCH PREPARATION COMPRISING DRUG, ORGANIC SOLVENT, LIPOPHILIC MASS BASE, AND POWDER

TECHNICAL FIELD

The present invention relates to a composition for a patch preparation comprising a drug, an organic solvent, a lipophilic mass base, and a powder. Particularly, the present invention relates to a composition for a patch preparation with the improved drug-solubility and the improved transdermal-absorbability, wherein the organic solvent comprises a fatty acid-based ionic liquid.

BACKGROUND ART

In order to prepare a composition for a patch preparation comprising a drug, the process of dissolving a drug in a solvent such as an organic solvent, mixing the drug solution with an adhesive, and extending the mixture to prepare a composition for a patch preparation has been generally used. In such case, the organic solvent used therein has been employed for serving as a transdermal absorption accelerator along with dissolving a drug.

Recently, some attempts to use a fatty acid-based ionic liquid as a solution for dissolving a drug or a transdermal absorption accelerator have been made (e.g. Patent Document 1). The ionic liquid used therein is mainly an alkanolamine salt of a fatty acid. Thus, the development as a non-aqueous patch preparation (a tape preparation) has been mainly studied to exert the effect of the ionic liquid.

On the other hand, a mass base used in such non-aqueous patch preparation (a tape preparation) is a lipophilic mass base which has less affinity for a fatty acid based-ionic liquid with high polarity in a salt form, and thus it has a tendency to be less miscible with the ionic liquid. As a result, a drug solution in which a drug is dissolved in a fatty acid based-ionic liquid alone or an organic solvent containing a fatty acid based-ionic liquid is less soluble and less miscible with a lipophilic mass base for a patch preparation, and thus has a tendency to be basically separated.

Hence, it has been known that when a non-aqueous patch preparation (a tape preparation) is prepared by using a drug solution prepared from a drug and an organic solvent containing a fatty acid-based ionic liquid, the drug solution comprising the fatty acid-based ionic liquid exudes onto the surface of the tape preparation, which can make the adhesibility to the skin poor. In addition, the drug solution can be encompassed into a lipophilic mass base in the form of droplets depending on the viscosities of the Lipophilic mass base and the drug solution comprising an ionic liquid and an organic solvent, the surfactant action of the ionic liquid, or the amount of the ionic liquid. In such case, the droplets are dispersed as separate vacuole, and thus the drug solution is not released from the mass base. As a result, this causes a variety of problems, for example, deterioration of the release property of a drug in the patch preparation.

Although a variety of means for solving these problems have been studied until now, any drastic means have not been found.

PRIOR ART DOCUMENTS

Patent Documents

Patent Document 1: JP 2009-066457

SUMMARY OF INVENTION

Problem to be Solved by the Invention

An object of the present invention is to provide a composition for a non-aqueous patch preparation which suitably disperses an organic solvent containing a drug into a lipophilic mass base for a non-aqueous patch preparation (a tape preparation), avoids the separate vacuolation of a drug solution, and further improves the adhesibility of the patch preparation and the release property of the drug. Particularly, the object is to provide a composition for a non-aqueous patch preparation in which a solvent containing an ionic liquid is used as an organic solvent.

Means for Solving the Problems

The present inventors have found that by adding a powder which is insoluble both in an ionic liquid or a solvent, and in a lipophilic mass base to a conventional non-aqueous patch preparation (a tape preparation) comprising an ionic liquid, a drug solution containing a drug is retained in spaces between the powders or in spaces between the powder and the mass base, and thus the drug solution is not released from the mass base. As a result, the present inventors have found that the drug solution does not uselessly exude onto the surface of the patch preparation, and thus the adhesibility of the patch preparation can be improved. In addition, the present inventors have found that the drug solution retained in the spaces between the powders or in the spaces between the powder and the mass base as described above can gradually transfer to the surface of the mass base via each space, and thus the release property of the drug can be improved. Also, even when an ionic liquid is encompassed into a lipophilic mass base as droplets, the drug solution can be released onto the surface of the mass base via the spaces between the powders or the spaces between the powder and the mass base which are formed by the addition of the powder, and thus the release property of the drug can be improved.

Furthermore, the present inventors have studied a variety of powders which could easily form the spaces between the powders or the spaces between the powder and the mass base, and then have found that inorganic fillers or organic reagents such as starch, crystalline cellulose, and agar which are contained in the patch preparation can produce useful effects. In addition, the present inventors have found that the sustained release of a drug can be achieved by a combination of these powders.

The present inventors have completed the present invention on the basis of the above findings.

The subject matters of the present invention are as follows.

(1) A composition for a non-aqueous patch preparation comprising a drug, an organic solvent, a lipophilic mass base, and a powder.

(2) The composition according to the above item (1), wherein the powder is insoluble both in the drug solution in the organic solvent and in the lipophilic mass base.

(3) The composition according to the above item (1), wherein the powder is at least one selected from the group consisting of crystalline cellulose, anhydrous silicic acid, starch, carmellose, carmellose metal salt, kaolin, agar, carrageenan, pectin, powdered sugar, polyethylene powder, and polystyrene sulfonate.

(4) The composition according to the above item (1) or (2), wherein the powder is crystalline cellulose.

(5) The composition according to any one of the above items (1) to (4), wherein the organic solvent comprises an ionic liquid.
(6) The composition according to the above item (5), wherein the ionic liquid is an alkanolamine organic carboxylase.
(7) The composition according to the above item (6), wherein said organic carboxylic acid is a combination of a higher fatty acid and an organic carboxylic acid having 3 to 7 carbon atoms.
(8) The composition according to the above item (7), wherein said higher fatty acid is a saturated or unsaturated fatty acid having 10 to 22 carbon atoms.
(9) The composition according to the above item (8), wherein said saturated or unsaturated fatty acid having 10 to 22 carbon atoms is at least one selected from the group consisting of decanoic acid, oleic acid, isostearic acid, and myristic acid.
(10) The composition according to the above item (7), wherein said organic carboxylic acid having 3 to 7 carbon atoms is a carboxylic acid compound having a hydroxyl group and a ketone group.
(11) The composition according to the above item (10), wherein said carboxylic acid compound having a hydroxyl group and a ketone group is at least one selected from the group consisting of lactic acid, levulinic acid, and salicylic acid.
(12) The composition according to the above item (6), wherein said alkanolamine is at least one selected from the group consisting of triethanolamine, triisopropanolamine, and diisopropanolamine.
(13) The composition according to the above item (5), wherein said ionic liquid is at least one selected from the group consisting of triethanolamine lactate, triisopropanolamine lactate, triethanolamine levulinate, diisopropanolamine levulinate, triisopropanolamine decanoate, triethanolamine salicylate, diisopropanolamine oleate, triethanolamine isostearate, diisopropanolamine isostearate, and diisopropanolamine myristate.
(14) The composition according to the above item (7), wherein said ionic liquid of an alkanolamine salt of organic carboxylic acid having 3 to 7 carbon atoms is at least one selected from the group consisting of triethanolamine lactate, triisopropanolamine lactate, triethanolamine levulinate, diisopropanolamine levulinate, triethanolamine salicylate, and triisopropanolamine salicylate.
(15) The composition according to the above item (8), wherein said ionic liquid of an alkanolamine salt of saturated or unsaturated fatty acid having 10 to 22 carbon atoms is at least one selected from the group consisting of triisopropanolamine decanoate, triethanolamine decanoate, diisopropanolamine decanoate, diisopropanolamine oleate, triethanolamine isostearate, diisopropanolamine isostearate, and diisopropanolamine myristate.
(16) The composition according to any one of the above items (1) to (15), wherein the elastomer of said lipophilic mass base is styrene-isoprene-styrene block copolymer.
(17) The composition according to any one of the above items (1) to (16), wherein said drug is selected from a small molecular medicinal compound, a protein medicine, an antigen peptide, or a nucleic acid derivative.

Effects of the Invention

The composition for a non-aqueous patch preparation of the present invention relates to a non-aqueous patch preparation (a tape preparation) comprising a drug solution in which a drug is dissolved in an organic solvent and an ionic liquid, a lipophilic mass base, and a powder. By the addition of the powder, said drug solution with high polarity can be retained in the spaces between the powders formed in the lipophilic mass base to avoid releasing the drug solution from the lipophilic mass. As a result, the deterioration of the adhesibility of the tape preparation can be prevented. In addition, the release property and the effective utilization ratio of a drug can be improved because the routes for releasing the drug solution out of the mass base via said spaces are made.

As described above, the release property of a drug which has been a problem in conventional tape preparations can be greatly improved, and also the adhesibility of tape preparations can be improved. Thus, such long-time sustention of the adhesibility of tape preparations enables the improvement of the transdermal absorbability and the sustained release of a drug. In addition, the effective utilization ratio of a drug can be improved along with the sustained release of a drug because the drug solution in the mass base gradually exudes onto the surface of the mass base via the spaces between the powders.

BRIEF DESCRIPTION OF DRAWINGS

FIG. 1 is a conceptual diagram showing a cross-section of the mass base in the non-aqueous patch preparation (the tape preparation) of the present invention. FIG. 1 shows that the powder is dispersed into the lipophilic mass base (the oil-soluble mass base), and the drug solution is retained in the spaces between the powders or in the spaces between the powder and the mass base. Furthermore, FIG. 1 shows that quite-narrow channels for releasing the drug solution from the inside of the mass base onto the surface of the mass base are formed by connecting these spaces to each other. The parts in which the powder is present on the surface of the mass base cause the exudation of the drug solution from the spaces around the powder, whereas the parts in which the powder is not present on the surface of the mass base cause less exudation or less release of the drug solution. As result, the deterioration of the adhesibility of the patch preparation is prevented as a whole. FIG. 1 also shows the above.

DESCRIPTION OF EMBODIMENTS

The term "drug" in the present invention denotes a drug for medical use selected from a small molecular medicinal compound, a protein medicine, an antigen peptide, or a nucleic acid derivative. Many of the drugs used in the present invention have hydrophilic residue(s) as a main substituent (or drugs in a salt form). Thereby, such drugs are less soluble in a lipophilic mass base. Thus, an ionic liquid with high polarity is used to dissolve the drug, and the solution of the drug in an ionic liquid is used as a drug solution. Among the drugs of the present invention, for example, a small molecular medicinal compound denotes a drug that exhibits acidity ("acidic drug") or a drug that exhibits basicity ("basic drug").

The term "acidic drug" herein denotes a drug which has a carboxylic acid as a functional group and exhibits acidity as a whole of the compound. Examples of the acidic drug include non-steroid anti-inflammatory drugs (NSAIDs) such as indomethacin, ketoprofen, ibuprofen, flurbiprofen, diclofenac, etodolac, and loxoprofen; anti-allergic drugs such as tranilast, cromoglicic acid, and pemirolast; sedative hypnotic drugs or anti-anxiety drugs such as amobarbital, secobarbital, and phenobarbital; and muscle relaxant drugs such as dantrolene, and mivacurium. Preferred examples of the acidic drug include indomethacin, flurbiprofen, ketoprofen, etodolac, ibuprofen, loxoprofen, and diclofenac.

The term "basic drug" in the present invention denotes a drug which has a primary, secondary, or tertiary amine structure as a functional group and exhibits basicity as a whole of the compound. Examples of the basic drug include topical anesthetic drugs such as lidocaine, dibucaine, bupivacaine, procaine, mepivacaine, bupivacaine, and tetracaine; anti-histamine drugs such as diphenhydramine; analgesic drugs such as tramadol; anti-spasmodic drugs such as eperisone; muscle relaxant drugs such as tolperisone; antitussive drugs such as dextromethorphan; acetylcholine decomposition inhibitors such as donepezil; and opioid analgesic drugs such as morphine, codeine, naloxone, fentanyl, and oxycodone. Preferred examples of the basic drug include lidocaine, tolperisone, bupivacaine, eperisone, tramadol, morphine, and donepezil.

The term "protein medicine" in the present invention denotes a protein for medical use. Examples of the protein medicine include various recombinant proteins and modified proteins which are relatively small molecules. Examples of various recombinant proteins and modified proteins include insulin, human growth hormone, elcatonin, calcitonin, EGF, VEGF, and GLP-1.

The term "antigen peptide" in the present invention denotes an antigenic fragment derived from a foreign microbe or a tumor cell which is used for stimulating immunity. Examples of the antigen peptide include WT-1, and human papillomavirus.

The term "nucleic derivative" in the present invention denotes a general term for DNA and RNA which are used as a medicinal ingredient. The DNA used herein is not especially limited as long as it is DNA for gene therapy. Examples of the nucleic derivative include DNA vaccine, antisense, ribozyme, aptamer, and siRNA.

The term "ionic liquid" in the present invention denotes a Brønsted salt prepared from a compound having carboxyl group(s) (an organic carboxylic acid) and an amine compound, which is in a viscous liquid form at ordinary temperature. Preferably, the amine compound is an alkanolamine.

The term "organic carboxylic acid" in the present invention denotes a higher fatty acid, an organic carboxylic acid having 3 to 7 carbon atoms, and a mixture thereof. Furthermore, the organic carboxylic acid-based ionic liquid denotes an alkanolamine salt of said organic carboxylic acid, that is, an alkanolamine salt of said higher fatty acid, an alkanolamine salt of said organic carboxylic acid having 3 to 7 carbon atoms, and a mixture thereof.

Preferably, in order to enhance the skin permeability of the drug, the organic carboxylic acid-based ionic liquid used in the drug solution is in the state that the drug solubility of the drug solution is close to saturation. Hence, the drug solubility of the drug solution can be controlled through a combination of the organic carboxylic acid-based ionic liquids and/or the selected solvent. For example, the drug solubility of the drug solution can be controlled by evaluating each drug solubility of the alkanolamine salt of said higher fatty acid and the alkanolamine salt of said organic carboxylic acid having 3 to 7 carbon atoms, and then mixing said salts.

The term "higher fatty acid" in the present invention denotes a saturated or unsaturated aliphatic carboxylic acid having 10 to 22 carbon atoms. Examples of the higher fatty acid include decanoic acid, oleic acid, and isostearic acid. Also, one or more of the higher fatty acids may be used in combination.

The term "organic carboxylic acid having 3 to 7 carbon atoms" in the present invention denotes a $C_{3-7}$ carboxylic acid compound having hydroxyl group(s) and ketone group(s). Examples of the organic carboxylic acid having 3 to 7 carbon atoms include lactic acid, levulinic acid, and salicylic acid. Also, one or more of the organic carboxylic acids may be used in combination.

The term "alkanolamine" in the present invention denotes an alkanolamine having 4 to 12 carbon atoms. Examples of the alkanolamine include diethanolamine, triethanolamine, diisopropanolamine, and triisopropanolamine.

The organic carboxylic acid-based ionic liquid of the present invention comprises an equilibrium mixture of each equimolar amount of an organic carboxylic acid and an amine compound along with a Brønsted salt. Preferred examples of the organic carboxylic acid-based ionic liquid of the present invention include triethanolamine lactate, triisopropanolamine lactate, triethanolamine salicylate, triisopropanolamine salicylate, triisopropanolamine decanoate, triethanolamine decanoate, diisopropanolamine decanoate, diisopropanolamine oleate, triethanolamine isostearate, diisopropanolamine isostearate, and a mixture thereof.

The term "drug solution" in the present invention denotes a solution in which a main drug (a drug) is dissolved in an organic solvent. Also, the drug solution denotes a solution further comprising an ionic liquid as a solubilizing agent of the drug or a transdermal absorption accelerator. The drug solution of the present invention typically comprises an ionic liquid with high drug solubility. Also, the organic solvent used therein is required to be miscible with the ionic liquid. Thus, a polar organic solvent can be typically used. For example, alcohols such as propylene glycol and/or esters such as diethyl sebacate and isopropyl myristate can be used. The drug solution of the present invention tends to be not so soluble in a lipophilic mass base (an oil-soluble mass base).

The term "powder" in the present invention denotes a solid powdered reagent which is insoluble and immiscible both in a drug solution and in a lipophilic mass base (an oil-soluble mass base). That is, the powder is a solid powdered reagent which is insoluble in a solvent such as an organic solvent in the drug solution even though the powder swells due to absorption of it. Examples of the powder include solid powdered reagents (fillers) used in a mass base in a patch preparation such as anhydrous silicic acid, crystalline cellulose, zinc oxide, titanium oxide, kaolin, and calcium carbonate. Furthermore, examples of the powder include flour, starch powder such as corn starch, carmellose, carmellose metal salt, agar, carrageenan, pectin, powdered sugar, polyethylene powder, and polystyrene sulfonate. Preferred examples of the powder include crystalline cellulose, anhydrous silicic acid, starch, carmellose, and carmellose metal salt. The adhesibility of the patch preparation is improved with increasing the amount of the powder of the present invention. Meanwhile, when the powder is excessive in amount, the patch preparation becomes hard, and deteriorates the adhesibility of the patch preparation. The amount of the powder to be added is preferably 1-10% by weight, more preferably 2-6% by weight. Furthermore, in light of the spaces formed by the powder in the mass base, the powder to be added may be large in amount when the drug solution is presented in large amounts, or the powder to be added may be small in amount when the drug solution is presented in small amounts. For example, when the amount of the drug solution is assumed as 1, the amount of the powder can be preferably in the range of 0.1 to 0.4.

The spaces to be formed can be properly controlled by combining various powders having different bulk density. Thus, suitable combination of the powders can be prepared responding to the amounts of the mass base and the organic solvent. For example, the powder such as light anhydrous silicic acid, corn starch, and crystalline cellulose may be used in combination.

The term "powder which is insoluble both in the drug solution and in the lipophilic mass base" in the present invention means that a powder is insoluble both in an organic solvent and an ionic liquid, and in a lipophilic mass base so that the spaces between the powders formed in the lipophilic mass base can be retained. The term "insoluble" is used in the sense of insolubility, and means that 1 mg of a powder cannot be dissolved in 10 g of an organic solvent or a lipophilic mass base, according to the definition of solubility in U.S. (U.S. Pharmacopeia National Formulary).

The term "organic solvent" in the present invention denotes a solvent that is miscible with an ionic liquid, which is used for preparing a drug solution in which a drug is dissolved in combination with the ionic liquid. The organic solvent in the present invention can be used as a transdermal absorption accelerator. Furthermore, the organic solvent can be used for dispersing the organic carboxylic acid-based ionic liquid in which a drug is dissolved into the mass base. Examples of the organic solvent in the present invention include alcohols such as ethanol, propanol, and oleyl alcohol; polyalcohols such as ethylene glycol, propylene glycol, 1,3-butanediol, polyethylene glycol (macrogol), and glycerin; and esters such as diethyl sebacate, isopropyl myristate, propylene carbonate, and diisopropyl adipate. These organic solvents may be used in suitable combination to achieve the above purposes. More preferably, polyalcohols such as propylene glycol, 1,3-butanediol, and polyethylene glycol can be used in combination with esters such as diethyl sebacate, isopropyl myristate, and propylene carbonate.

The term "lipophilic mass base" in the present invention denotes a mass base (an adhesive) comprising a lipophilic macromolecule as a main component. The mass base is composed of an elastomer and a lipophilic (hydrophobic) adhesive, in which a drug solution is dispersed or emulsified. When the mass base is composed of an elastomer and a lipophilic (hydrophobic) adhesive, it can be used as a non-aqueous tape preparation (a plaster). When the mass base is composed of an elastomer and a hydrophilic adhesive, it can be used as an aqueous patch preparation (a cataplasm). As described above, the lipophilic mass base is composed of an elastomer, a tackifier, a softening filer, and the like.

Examples of the elastomer include synthetic rubbers such as styrene-isoprene-styrene copolymer (SIS), silicon rubbers, polyisobutylene, polystyrene-butadiene copolymer, and polyisobutylene; acrylic acid resins such as alkyl acrylate and alkyl methacrylate; and natural rubbers.

The tackifier denotes a reagent which can be added into the elastomer such as a SIS resin to enhance the adhesibility of a patch preparation to the skin. Examples of the tackifier include a polyterpene resin, a polyolefin resin (Plastibase®, and the like), a polystyrene resin, an aromatic petroleum resin, rosin, and hydrogenated rosin. Preferred examples of the tackifier include a polyterpene resin and a polyolefin resin (Plastibase®, and the like).

The softening agent is a reagent which can be added to make the elastomer such as SIS resin and the adhesive flexible. Examples of the softening agent include petroleum-based softening agents such as polybutene, polyisobutylene, and process oil; fatty oil-based softening agents such as palm oil and castor oil; purified lanolin; and liquid paraffin. Preferred examples of the softening agent include polybutene and liquid paraffin.

The patch preparation of the present invention may further comprise additives such as an antioxidant, a surfactant, a thickening agent, and a surfactant as long as the effects of the present invention are not prevented. As the suitable additives, commercially available reagents may be used for any purpose.

Examples of the antioxidant include organic antioxidants such as BHT, propyl gallate, and sodium ascorbate; and inorganic antioxidants such as sodium thiosulfate, sodium bisulfite, sodium sulfite, and sodium pyrosulfite.

In addition, a thickening agent such as Carbopol®, an ultraviolet absorbing agent, and/or powders may be added.

Examples of the surfactant can include a non-ionic surfactant, an anionic surfactant, a cationic surfactant, and an amphoteric surfactant. Examples of the non-ionic surfactant include sorbitan monolaurate, sorbitan monopalmitate, sorbitan sesquioleate, glycerin monostearate, decaglyceryl monolaurate, hexaglycerin polyricinoleate, polyoxyethylene (9) lauryl ether, polyoxyethylene (2) lauryl ether, polyoxyethylene (4,2) lauryl ether, polyoxyethylene (5) nonylphenyl ether, polyoxyethylene (7,5) nonylphenyl ether, polyoxyethylene (10) nonylphenyl ether, polyoxyethylene (3) octylphenyl ether, polyoxyethylene (10) octylphenyl ether, polyoxyethylene (10) oylelamine, polyoxy (5) oleylamine, polyoxy (5) oleic amide, polyoxyethylene (2) monolaurate, monoglyceride stearate, and polyoxyethylene castor oil (hydrogenated castor oil).

Examples of said anionic surfactant include sodium lauryl sulfate, potassium lauryl sulfate, triethanolamine lauryl sulfate, sodium cetyl sulfate, sodium lauroyl sarcosinate, sodium di-2-ethylhexyl sulfosuccinate, sodium polyoxyethylene (10) lauryl ether phosphate, sodium polyoxyethylene (4) lauryl ether phosphate, sodium polyoxyethylene (5) cetyl ether phosphate, and sodium polyoxyethylene (6) oleyl ether phosphate.

Examples of said cationic surfactant include stearyl trimethylammonium chloride, distearyl dimethylammonium chloride, benzalkonium chloride, and stearyl dimethyl benzylammonium chloride.

Examples of said amphoteric surfactant include betaine lauryldimethylaminoacetate and 2-alkyl-N-carboxymethyl-N-hydroxyethyl imidazolinium betaine. In addition to the above, lauroyl diethanolamide can also be used.

In addition, a thickening agent such as Carbopol®, an ultraviolet absorbing agent, and/or powders may be added.

The term "patch preparation" in the present invention denotes a non-aqueous patch preparation (a tape preparation) which does not contain water as an essential ingredient. As the mass base in the patch preparation of the present invention, conventional bases, for example, an acrylic acid resin base, or a base of a SIS resin which contains a tackifier, a softening agent and the like can be used. Preferred examples of the base include a base in which a SIS resin is used as an elastomer.

As a method for preparing the patch preparation of the present invention, methods similar to those for adhesive tapes may be adopted. Examples of the method include a solvent-coating method. Said solvent-coating method is a method which comprises preparing a mass base composition comprising a drug (a drug solution), and coating the composition directly on a backing support body followed by drying. Also, a method can be used which comprises once coating said mass base composition on a release paper followed by drying, and then removing the paper followed by contact-pressing the composition on the paper to the backing.

Said release paper can be used for protecting the adhesive layer. As examples of the paper, a polyethylene-coated quality paper, a polyolefin-coated glassine paper, a polyethylene terephthalate (hereinafter referred to as PET) film, a polypropylene film or the like, one side of which is treated with silicon, may be used.

EXAMPLES

Hereinafter, the present invention will be described more specifically with reference to Examples. However, the present invention is not intended to be limited to them by any means.

Example 1

Improvement of the Drug Release Property of Non-Aqueous Patch Preparation (Tape Preparation) by Addition of Powder a) Addition of Powder to Preparation in which Deterioration of the Release Property is Caused by Separate Vacuolation of Drug Solution (A)

Preparation Examples 1 and 2 are patch preparations comprising a drug solution consisting of only a drug and an ionic liquid. In order to make it easy to detect the release property of a drug, brilliant blue FCF was used as an alternative to the drug. The reagents were weighed according to the composition (part by weight) in Table 1 below to prepare the tape preparations for evaluation.

Specifically, brilliant blue FCF was dissolved in triethanolamine lactate, and then diisopropylamine isostearate was added thereto and mixed to prepare the drug solution. Following the conventional solvent method using toluene as a solvent, terpene resin, styrene-isoprene-styrene copolymer, butylhydroxytoluene, and liquid paraffin were dissolved in toluene, and then the drug solution was added thereto and mixed. Next, corn starch or light anhydrous silicic acid was added thereto and mixed, and then each mixture was coated on the silicone-coated PET film and dried. After removal of the toluene, the backing was laminated to prepare the preparations.

The prepared tape preparations were tested on the release property of brilliant blue FCF from the mass base. Specifically, the tape preparations of Preparation Examples and 2 and Comparison Example 1 were cut into 3×3 cm, dipped into a beaker containing 8 mL of purified water, and then incubated at 32° C. for 6 hours. Next, the emission of the blue pigment from the tape preparations of the examples was measured by the absorption spectrum measurement method at the wavelength of 630 nm. The results are also shown in Table 1 below.

TABLE 1

|  | Preparation Example 1 | Preparation Example 2 | Comparison Example 1 |
|---|---|---|---|
| Brilliant Blue FCF | 0.016 | 0.016 | 0.016 |
| Ionic Liquid: | | | |
| Triethanolamine Lactate | 12 | 12 | 12 |

TABLE 1-continued

|  | Preparation Example 1 | Preparation Example 2 | Comparison Example 1 |
|---|---|---|---|
| Diisopropanolamine Isostearate | 8 | 8 | 8 |
| Lipophilic Mass Base: | | | |
| Terpene Resin | 36 | 36 | 36 |
| Styrene-Isoprene-Styrene Copolymer | 20 | 20 | 20 |
| Antioxidant: | | | |
| Liquid Paraffin | 13 | 13 | 13 |
| Butylhydroxytoluene | 1 | 1 | 1 |
| Powder: | | | |
| Corn Starch | 10 | | |
| Light Anhydrous Silicic Acid | | 3 | |
| Release Test: | | | |
| Amount of Emission (Absorbance/Measurement Wavelength 630 nm) | 0.119 | 0.348 | 0.025 |

As shown in the above Table 1, the release property of the drug solution in the preparations of Preparation Examples 1 and 2 comprising the powder was improved by about 5 to 12 times as compared to that of the preparation of Comparison Example 1 without the powder. Also, the result suggests that anhydrous silicic acid can make a larger contribution to the spaces and the like as a powder than corn starch, and produce a greater release property of the drug solution.

b) Addition of Powder to Preparation in which Deterioration of the Release Property is Caused by Separate Vacuolation of Drug Solution (B)

As with the above a), in order to make it easy to detect the release property of a drug, brilliant blue FCF was used as an alternative to the drug. The reagents were weighed according to the composition (part by weight) in Table 2 below to prepare the tape preparations for evaluation.

Specifically, brilliant blue FCF was dissolved in triethanolamine lactate, and then macrogol 400 was added thereto and mixed to prepare a drug solution. Following the conventional solvent method using toluene as a solvent, terpene resin, styrene-isoprene-styrene copolymer, butylhydroxytoluene, and liquid paraffin were dissolved in toluene, and then the drug solution was added thereto and mixed. Next, crystalline cellulose or light anhydrous silicic acid was added thereto and mixed, and then each mixture was coated on the silicone-coated PET film and dried. After removal of the toluene, the backing was laminated to prepare the preparations.

The prepared tape preparations were tested on the release property of brilliant blue FCF from the mass base. Specifically, the preparations of Preparation Examples 3 and 4 and Comparison Example 2 were cut into 3×3 cm, dipped into a beaker containing 8 mL of purified water, and then incubated at 32° C. for 6 hours. Next, the emission of the blue pigment from the tape preparations of the examples was measured by the absorption spectrum measurement method at the wavelength of 630 nm. The results are also shown in Table 2 below.

TABLE 2

|  | Preparation Example 3 | Preparation Example 4 | Comparison Example 2 |
|---|---|---|---|
| Brilliant Blue FCF | 0.016 | 0.016 | 0.016 |
| Ionic Liquid: | | | |
| Triethanolamine Lactate | 6 | 6 | 6 |
| Organic Solvent: | | | |
| Macrogol 400 | 14 | 14 | 14 |
| Lipophilic Mass Base: | | | |
| Terpene Resin | 38 | 38 | 38 |
| Styrene-Isoprene-Styrene Block Copolymer | 20 | 20 | 20 |
| Antioxidant: | | | |
| Liquid Paraffin | 17 | 17 | 17 |
| Butylhydroxytoluene | 1 | 1 | 1 |
| Powder: | | | |
| Crystalline cellulose | 4 | | |
| Light Anhydrous Silicic Acid | | 4 | |
| Release Test: | | | |
| Amount of Emission (Absorbance/Measurement Wavelength 630 nm) | 0.027 | 0.356 | 0.005 |

Comparing the above Table 2 with Table 1, as shown in Comparison Examples 1 and 2, the release properties of the drug solutions greatly varied with the conditions such as the difference in the composition of the ionic liquid and the presence or absence of the organic solvent. On the other hand, as shown in Preparation Examples 2 and 4, the release properties of the drug solutions in the preparations comprising anhydrous silicic acid as the powder were almost identical. The results suggest that the drug solution can be released from the mass base without big influence, by mixing the powder (anhydrous silicic acid) to form the spaces in the mass base, even though the way to incorporate the drug solution into the mass base varies with the conditions such as the different composition of the ionic liquid, and the presence or absence of the organic solvent.

Also, the release property of the preparation comprising crystalline cellulose as the powder was shown to be improved by about 5 times as compared to that of the preparation without the powder.

Example 2

Improvement of the Adhesibility on Non-Aqueous Patch Preparation (Tape Preparation) by Addition of Powder a) Addition of Powder to Preparation Whose Adhesibility is Reduced and which Loosely Releases Drug Solution from Mass Base (A)

Preparation Examples 5 and 6 are patch preparations comprising only the ionic liquid without any drug, i.e., the preparations are prepared as a placebo because they are only for the evaluation about the adhesibility. The reagents were weighed according to the composition (part by weight) in Table 3 below to prepare the tape preparations for evaluation.

Specifically, triethanolamine lactate, triisopropanolamine lactate, diisopropanolamine isostearate, triisopropanolamine decanoate, triethanolamine salicylate, macrogol 400, and propylene carbonate were mixed to prepare the drug solution. Following the conventional solvent method using toluene as a solvent, styrene-isoprene-styrene copolymer, isopropyl myristate, butylhydroxytoluene, terpene resin, polybutene, and liquid paraffin were dissolved in toluene, and then the drug solution was added thereto and mixed. Next, light anhydrous silicic acid or crystalline cellulose was added thereto and mixed, and then each mixture was coated on the silicone-coated PET film and dried. After removal of the toluene, the backing was laminated to prepare the preparations.

TABLE 3

|  | Preparation Example 5 | Preparation Example 6 | Comparison Example 3 |
|---|---|---|---|
| Ionic Liquid: | | | |
| Triethanolamine Lactate | 6 | 6 | 6 |
| Triisopropanolamine Lactate | 1 | 1 | 1 |
| Diisopropanolamine Isostearate | 10 | 10 | 10 |
| Triisopropanolamine Decanoate | 2 | 2 | 2 |
| Triethanolamine Salicylate | 1 | 1 | 1 |
| Organic Solvent: | | | |
| Macrogol 400 | 2 | 2 | 2 |
| Propylene Carbonate | 5 | 5 | 5 |
| isopropyl Myristate | 20 | 20 | 20 |
| Antioxidant: | | | |
| Butylhydroxytoluene | 1 | 1 | 1 |
| Lipophilic mass Base: | | | |
| Terpene Resin | 24 | 24 | 24 |
| Polybutene | 1 | 1 | 1 |
| Styrene-Isoprene-Styrene Block Copolymer | 14 | 14 | 14 |
| Liquid Paraffin | 8 | 8 | 8 |
| Powder: | | | |
| Light Anhydrous Silicic Acid | 5 | | |
| Crystalline Cellulose | | 5 | | b) Addition of Powder to Preparation Whose Adhesibility is Reduced and which Loosely Releases Drug Solution from Mass Base (B)

As described above, the tape preparation of Preparation Example 7 was prepared to evaluate the adhesibility as described above, which had a different composition of the ionic liquid from that of Example 1. The reagents were weighed according to the composition (part by weight) in Table 4 below to prepare the tape preparations for evaluation.

Specifically, triethanolamine levulinate, triisopropanolamine levulinate, diisopropanolamine isostearate, triisopropanolamine decanoate, triethanolamine salicylate, macrogol 400, and propylene carbonate were mixed to prepare the drug solution. Following the conventional solvent method using toluene as a solvent, styrene-isoprene-styrene copolymer, isopropyl myristate, butylhydroxytoluene, terpene resin, polybutene, and liquid paraffin were dissolved in toluene, and then the drug solution was added thereto and mixed. Next, light anhydrous silicic acid or crystalline cellulose was added thereto and mixed, and then each mixture was coated on the silicone-coated PET film and dried. After removal of the toluene, the backing was laminated to prepare the preparations.

TABLE 4

|  | Preparation Example 7 | Comparison Example 4 |
|---|---|---|
| Ionic Liquid: | | |
| Triethanolamine Levulinate | 6 | 6 |
| Triisopropanolamine Levulinate | 1 | 1 |
| Diisopropanolamine Isostearate | 10 | 10 |
| Triisopropanolamine Decanoate | 2 | 2 |
| Triethanolamine Salicylate | 1 | 1 |
| Organic Solvent: | | |
| Macrogol 400 | 2 | 2 |
| Propylene Carbonate | 5 | 5 |
| Isopropyl Myristate | 20 | 20 |
| Antioxidant: | | |
| Butylhydroxytoluene | 1 | 1 |
| Lipophilic Mass Base: | | |
| Terpene Resin | 24 | 24 |
| Polybutene | 1 | 1 |
| Styrene-Isoprene-Styrene Block Copolymer | 14 | 14 |
| Liquid Paraffin | 8 | 8 |
| Power: | | |
| Crystalline Cellulose | 5 | | c) Results of Test for Evaluating the Adhesibility

The adhesibility test was performed following the ball tack test as defined by JIS. The patch preparation is deemed to have sufficient adhesibility when stopping ball No. 4. Thus, the ball tack test was performed using ball No. 4. Preparation Examples 5, 6 and 7 as well as Comparison Examples 3 and 4 were tested as test samples.

The results are shown in Table 5 below.

TABLE 5

|  | Stopping of Steel Ball No. 4 |
|---|---|
| Preparation Example 5 | Stopped |
| Preparation Example 6 | Stopped |
| Preparation Example 7 | Stopped |
| Comparison Example 3 | Not stopped |
| Comparison Example 4 | Not stopped |

The above preparations of Comparison Examples 3 and 4 were beginning to loosely release the drug solution on the surface of the mass base in the patch preparations, and thereby it was observed that the adhesibility of the patch preparations was deteriorated. On the other hand, the preparations of Preparation Examples 5 and 7 comprising the powder did not cause the phenomenon such as the loose exudation of the drug solution. Thus, it was shown that the adhesibility of the preparation examples was not deteriorated.

Example 3

Improvement of the Transdermal Absorbability and Adhesibility of Non-Aqueous Patch Preparation (Tape Preparation) Comprising Oxycodone Hydrochloride, Organic Solvent Containing Ionic Liquid, and Powder a) Improvement of the Transdermal Absorbability The transdermal absorbability of the tape preparation is supposed to be improved by the improvement of the release property of the drug from the mass base of the tape preparation. In order to confirm it, the reagents were weighed according to the composition (part by weight) in Table 6 below to prepare tape preparations comprising oxycodone hydrochloride as the drug.

Specifically, oxycodone hydrochloride trihydrate was used as the drug, and decanoic acid, isostearic acid, myristic acid, oleic acid, and diisopropanolamine were mixed to prepare a combined ionic liquid. To the combined ionic liquid were added macrogol 400, propylene carbonate, ascorbic acid, and oxycodone hydrochloride hydrate to prepare the drug solution. Following the conventional solvent method using toluene as a solvent, styrene-isoprene-styrene copolymer, diethyl sebacate, isopropyl myristate, butylhydroxytoluene, terpene resin, polybutene, liquid paraffin, and gel hydrocarbon were dissolved in toluene, and then the drug solution was added thereto and mixed. Next, light anhydrous silicic acid was added thereto and mixed, and then each mixture was coated on the silicone-coated PET film and dried. After removal of the toluene, the backing was laminated to prepare the preparations.

The skin permeability test on the prepared tape preparations was performed using a Franz Cell. The results are also shown in Table 6.

TABLE 6

|  | Preparation Example 8 | Comparison Example 5 |
|---|---|---|
| Oxycodone Hydrochloride Hydrate | 2.3070 | 2.3070 |
| Ionic Liquid: | | |
| Decanoic Acid | 0.975 | 0.975 |
| Isostearic Acid | 6.00 | 6.00 |
| Myristic Acid | 0.40 | 0.40 |
| Oleic Acid | 0.80 | 0.80 |
| Diisopropanolamine | 1.646 | 1.646 |
| Organic Solvent: | | |
| Propylene Glycol | 14.50 | 14.50 |
| Propylene Carbonate | 10.00 | 10.00 |
| Diethyl Sebacate | 5.00 | 5.00 |
| Isopropyl Myristate | 3.00 | 3.00 |
| Antioxidant: | | |
| Butylhydroxytoluene | 1.00 | 1.00 |
| Ascorbic acid | 0.10 | 0.10 |
| Lipophilic Mass Base: | | |
| Terpene Resin | 27.00 | 27.00 |
| Styrene-Isoprene-Styrene Block Copolymer | 15.00 | 15.00 |

TABLE 6-continued

|  | Preparation Example 8 | Comparison Example 5 |
| --- | --- | --- |
| Gel Hydrocarbon | 5.00 | 5.00 |
| Liquid Paraffin | 3.272 | 3.272 |
| Powder: | | |
| Light Anhydrous Silicic Acid | 4.00 | 0.00 |
| Total (%) | 100.000 | 96.000 |
| Skin Permeation Amount (µg/cm$^2$) | 64.8 | 40.2 |
| Two hours | | |
| Four hours | 160.3 | 121.9 | b) Improvement of the Adhesibility of Preparation

The adhesibility test was performed following the ball tack test as defined by JIS. The ball tack test was performed using variously-numbered balls. Preparation Example 8 and Comparison Example 5 were tested as test samples. The results are shown in Table 7 below.

TABLE 7

| Number of Ball | Preparation Example 8 | Comparison Example 5 |
| --- | --- | --- |
| No. 1 | — | ○ |
| No. 2 | — | ○ |
| No. 3 | ○ | x |
| No. 4 | ○ | x |
| No. 5 | ○ | — |
| No. 6 | ○ | — |
| No. 7 | ○ | — |
| No. 8 | ○ | — |
| No. 9 | ○ | — |
| No. 10 | ○ | — |
| No. 11 | ○ | — |
| No. 12 | ○ | — |
| No. 13 | ○ | — |
| No. 14 | ○ | — |
| No. 15 | x | — |

[NOTE]
○: Stopped,
X: Not stopped,
—: No test

The bigger number of the ball is the bigger size, i.e., the heavier ball. Stopping the motion of a heavier ball means that the preparation has a higher adhesibility. As shown in the above Table 7, the patch preparation of Preparation Example 8 can stop the heavy ball No. 14. On the other hand, the patch preparation of Comparison Example 5 can stop only light balls up to No. 2. The difference shows that the loose exudation of the drug solution on the surface of the mass base greatly varies with the presence or absence of the powder (anhydrous silicic acid). That is, it is shown that the drug solution is hard to exude from the mass base in the preparation by mixing the powder, and thus the adhesibility of the preparation is not deteriorated.

The loose exudation of the drug solution as described above in the patch preparation of Comparison Example 5 which comprises no powder means that the drug solution which is not sufficiently dispersed into the mass base transfers to the surface of the mass base. However, the transfer of the drug solution to the surface leads to a good result from the viewpoint of the release property of the drug solution. That is, the preparation has a poor adhesibility, but an excellent release property of the drug solution. When the release property of the drug solution is excellent, the transdermal absorbability of the drug also shows a good result.

On the other hand, as shown in Preparation Example 8, the drug solution can be absorbed and retained in the spaces within the mass base by the addition of the powder (anhydrous silicic acid), and thereby the patch preparation can ensure the release property of the drug solution in addition to the improvement and retainment of the adhesibility of the preparation. As a result, the transdermal absorbability can be improved. For example, comparing Preparation Example 8 with Comparison Example 5, the skin permeability of the drugs in Preparation Example 8 after 4 hour was about 1.3 times better than that of Comparison Example 5. As a result, it was demonstrated that the patch preparation of Preparation Example 8 comprising the powder led to a better balance between the adhesibility and the release property of the drug.

Test Example 1

In Vitro Skin Permeability Test

The test to evaluate the transdermal absorbability of oxycodone in the patch preparation of Example 3 was performed using a Franz diffusion cell (permeable area: cm$^2$, volume of receptor solution: 8 mL) at the test temperature of 32° C. as follows:
(1) Rat's skin: skin isolated from the abdomen of a 5-week old Wistar rat (male)
(2) Receptor solution: physiological saline+10% ethanol
(3) Concentration measurement of the permeable drug: HPLC The commercially available rat's abdominal frozen skin (5-week old Wistar rat) was mounted in a vertical diffusion cell (effective diffusion area: 1 cm$^2$). Each sample in Table 6 (Preparation Example 8 and Comparison Example 5) was applied to the stratum corneum side, and also physiological saline+10% ethanol were applied to the dermic layer side. The skin permeability of the drug was measured by HPLC to determine the cumulative permeation amount of the drug at 2 hours and 4 hours. As a result, the transdermal absorbability of oxycodone as shown in Table 6 was evaluated.

Test Example 2

Test for Evaluating the Adhesibility

The adhesibility test was performed following the ball tack test as defined by JIS. The patch preparation is deemed to have sufficient adhesibility when stopping ball No. 4. Thus, the ball tack test was performed using ball No. 4. Preparation Examples 5-8 and Comparison Examples 3-5 were tested as test samples.

Also, Preparation Example 8 and Comparison Example 5 were evaluated up to ball No. 15, besides ball No. 4.

Example 4

Preparation of Non-Aqueous Patch Preparation Comprising Lidocaine Salt of Etodolac, Organic Solvent Containing Ionic Liquid, and Powder In the same manner as Example 3, the reagents were weighed according to the composition (part by weight) in Table 8 below to prepare the tape preparations comprising the lidocaine salt of etodolac as the drug.

Specifically, etodolac-lidocaine salt was added to propylene glycol and mixed to prepare the drug solution. Following the conventional solvent method using toluene as a solvent, diethyl sebacate, butylhydroxytoluene, terpene resin, styrene-isoprene-styrene copolymer, and liquid paraffin were dissolved in toluene, and then the drug solution was added thereto and mixed. Next, crystalline cellulose or light anhydrous silicic acid was added thereto and mixed, and then each mixture was coated on the silicone-coated PET film and dried. After removal of the toluene, the backing was laminated to prepare the preparations.

As with Example 3, the in vitro skin permeability test of etodolac and the test for evaluating the adhesibility of the prepared patch preparations were performed. The results are also shown in Table 8.

TABLE 8

|  | Preparation Example 9 | Preparation Example 10 |
|---|---|---|
| Etodolac-Lidocaine Salt | 4.4 | 4.4 |
| Organic Solvent: |  |  |
| Propylene glycol | 4 | 4 |
| Diethyl Sebacate | 4 | 4 |
| Antioxidant: |  |  |
| Butylhydroxytoluene | 1 | 1 |
| Lipophilic Mass Base: |  |  |
| Terpene Resin | 20 | 20 |
| Styrene-Isoprene-Styrene Block Copolymer | 40 | 42 |
| Liquid Paraffin | 20.6 | 19.6 |
| Powder: |  |  |
| Light Anhydrous Silicic Acid | 4 |  |
| Crystalline Cellulose |  | 7 |
| Skin Permeation Amount ($\mu g/cm^2/6\ hr$) | 20.7 | 25.6 |
| Adhesibility Test, Stopping of Ball No. 4 | Stopping | Stopping |

As shown in the above Table 8, the patch preparations of Preparation Examples 9 and 10 can produce a better transdermal absorbability of etodolac as well as a better adhesibility by the addition of the powder.

Example 5

Preparation of Non-Aqueous Patch Preparation Comprising Calcitonin, Organic Solvent Containing Ionic Liquid, and Powder In the same manner as Example 3, the reagents were weighed according to the composition (part by weight) in Table 9 below to prepare the tape preparations comprising calcitonin as the drug.

Calcitonin salmon was dissolved in triethanolamine levulinate or triethanolamine lactate, and then triethanolamine isostearate, macrogol 400, propylene carbonate, and propylene glycol were added thereto and mixed to prepare each drug solution. Following the conventional solvent method using toluene as a solvent, diethyl sebacate, terpene resin, styrene-isoprene-styrene copolymer, and liquid paraffin were dissolved in toluene, and then the drug solution was added thereto and mixed. Next, corn starch, crystalline cellulose or light anhydrous silicic acid was added thereto and mixed, and then each mixture was coated on the silicone-coated PET film and dried. After removal of the toluene, the backing was laminated to prepare the preparations.

TABLE 9

|  | Preparation Example 11 | Preparation Example 12 |
|---|---|---|
| Calcitonin | 0.1 | 0.1 |
| Ionic Liquid: |  |  |
| Triethanolamine Levulinate | 4 |  |
| Triethanolamine Lactate |  | 4 |
| Triethanolamine Isostearate | 2 | 3 |
| Organic Solvent: |  |  |
| Macrogol 400 | 9 | 7 |
| Propylene Carbonate | 3 | 7 |
| Propylene Glycol | 8 | 5 |
| Diethyl Sebacate | 3 | 4 |
| Lipophilic Mass Base: |  |  |
| Styrene-Isoprene-Styrene Block Copolymer | 16 | 16 |
| Terpene Resin | 35 | 36 |
| Liquid Paraffin | 11.9 | 12.9 |
| Powder: |  |  |
| Starch | 8 |  |
| Light Anhydrous Silicic Acid |  | 5 |

The adhesibility and drug-transdermal-absorbability of the patch preparations of Preparation Examples 11 and 12 can be improved by the addition of the powder.

Example 6

Preparation of Non-Aqueous Patch Preparation Comprising Agomelatine, Organic Solvent Containing Ionic Liquid, and Powder In the same manner as Example 3, the reagents were weighed according to the composition (part by weight) in Table 10 below to prepare the tape preparations comprising agomelatine as the drug.

Specifically, agomelatine was added to the ionic liquid and mixed to prepare the drug solution. Following the conventional solvent method using toluene as a solvent, the organic solvent, the antioxidant, the lipophilic mass base, and the drug solution were mixed. Next, crystalline cellulose and light anhydrous silicic acid were added thereto and mixed, and then each mixture was coated on the silicone-coated PET film and dried. After removal of the toluene, the backing was laminated to prepare the preparations.

As with Example 3, the in vitro skin permeability test was performed on the prepared patch preparations. The results are also shown in Table 10.

TABLE 10

|  | Comparison Example 6 | Preparation Example 13 |
|---|---|---|
| Agomelatine | 1.0 | 1.0 |
| Ionic Liquid: |  |  |
| Triethanolamine Isostearate | 2.5 | 2.5 |

TABLE 10-continued

|  | Comparison Example 6 | Preparation Example 13 |
|---|---|---|
| Triethanolamine Lactate | 1.5 | 1.5 |
| Organic Sovent: | | |
| Isopropyl Myristate | 3.8 | 3.8 |
| Propyl Carbonate | 6.0 | 5.0 |
| Polyethylene glycol | 6.0 | 5.0 |
| Kollidon K90 | 0.5 | 0.5 |
| Oleic Acid | 1.9 | 1.9 |
| Antioxidant: | | |
| Butylhydroxytoluene | 1.0 | 1.0 |
| Lipophilic Mass Base: | | |
| Terpene Resin | 36.3 | 35.3 |
| Styrene-Isoprene-Styrene Block Copolymer | 20.0 | 19.0 |
| Liquid Paraffin | 19.5 | 19.5 |
| Powder: | | |
| Light Anhydrous Silicic Acid | | 1.0 |
| Crystalline Cellulose | | 3.0 |
| Skin Permeation Amount ($\mu g/cm^2/6$ hr) | 9.1 | 26.7 |

As shown in the above results of Preparation Examples 13 and 14, the transdermal absorbability of agomeltatine in the patch preparation comprising the powder could be improved by about 3 times.

In addition, the measured residual ratio of the drug in the preparation was 40%. As a result, it was shown that the preparation example produced an excellent effect that about 60% of the drug used was transdermally absorbed.

INDUSTRIAL APPLICABILITY

The non-aqueous patch preparation of the present invention comprising a powder ingredient has the improved adhesibility since the powder ingredient can make spaces in a lipophilic mass base, wherein a drug solution is retained once and then gradually released. In addition, both of the adhesibility of the patch preparation and the release property of the drug solution, which are conflicting factors in normal tape preparations, can be improved in the present invention, and thus the transdermal absorbability of the drug can also be maintained and improved. Thus, the patch preparation of the present invention has an excellent adhesibility to the skin and further an improved transdermal absorbability of the drug. Also, the patch preparation can sustainedly release the drug since the drug solution is gradually released from the spaces between the powders. As a result, the present invention has made it possible to expand the use to new ones (the expansion of the intended drugs) in the non-aqueous patch preparation comprising an ionic liquid, and thus has also made it possible to expand the possibility of treating diseases with the patch preparation.

The invention claimed is:

1. A non-aqueous patch preparation comprising
a drug solution in which a drug is dissolved in an ionic liquid,
a lipophilic mass base, and
anhydrous silicic acid powders that are insoluble both in the ionic liquid and in the lipophilic mass base,
wherein the drug solution is retained in spaces between the powders or in spaces between the powders and the lipophilic mass base, and
the patch preparation has 2% to 10% by weight of the anhydrous silicic acid powders.

2. A non-aqueous patch preparation comprising
a drug solution in which a drug is dissolved in an ionic liquid,
a lipophilic mass base, wherein the drug or the drug solution is insoluble in the lipophilic mass base, and
anhydrous silicic acid powders that are insoluble both in the ionic liquid and in the lipophilic mass base,
wherein the patch preparation has 2% to 10% by weight of the anhydrous silicic acid powders.

3. A non-aqueous patch preparation comprising
a drug solution in which a drug is dissolved in an ionic liquid,
a lipophilic mass base, and
anhydrous silicic acid powders that are insoluble both in the ionic liquid and in the lipophilic mass base, wherein the amount of the powders is 0.1 to 0.4 times the amount of the drug solution,
wherein the drug solution is released via spaces between the powders or spaces between the powders and the lipophilic mass base, and
the patch preparation has 2% to 10% by weight of the anhydrous silicic acid powders.

4. The patch preparation according to claim 1, wherein the ionic liquid comprises one or more alkanolamine organic carboxylates.

5. The patch preparation according to claim 4, wherein said ionic liquid comprises (i) a first alkanolamine salt of a higher fatty acid and (ii) a second alkanolamine salt of an organic carboxylic acid having 3 to 7 carbon atoms.

6. The patch preparation according to claim 5, wherein said higher fatty acid is a saturated or unsaturated fatty acid having 10 to 22 carbon atoms.

7. The patch preparation according to claim 6, wherein said saturated or unsaturated fatty acid having 10 to 22 carbon atoms is at least one selected from the group consisting of decanoic acid, oleic acid, isostearic acid, and myristic acid.

8. The patch preparation according to claim 5, wherein said organic carboxylic acid having 3 to 7 carbon atoms is a carboxylic acid compound having a hydroxyl group and ketone group.

9. The patch preparation according to claim 8, wherein said carboxylic acid compound having a hydroxyl group and a ketone group is at least one selected from the group consisting of lactic acid, levulinic acid, and salicylic acid.

10. The patch preparation according to claim 4, wherein alkanolamine of said alkanolamine organic carboxylate is at least one selected from the group consisting of triethanolamine, triisopropanolamine, and diisopropanolamine.

11. The patch preparation according to claim 1, wherein said ionic liquid is at least one selected from the group consisting of triethanolamine lactate, triisopropanolamine lactate, triethanolamine levulinate, diisopropanolamine levulinate, triisopropanolamine decanoate, triethanolamine salicylate, diisopropanolamine oleate, triethanolamine isostearate, diisopropanolamine isostearate, and diisopropanolamine myristate.

12. The patch preparation according to claim 1, wherein said ionic liquid comprises at least one selected from the group consisting of triethanolamine lactate, triisopropanolamine lactate, triethanolamine levulinate, diisopropanolamine levulinate, triethanolamine salicylate, and triisopropanolamine salicylate.

13. The patch preparation according to claim 1, wherein said ionic liquid comprises at least one selected from the group consisting of triisopropanolamine decanoate, triethanolamine decanoate, diisopropanolamine decanoate, diisopropanolamine oleate, triethanolamine isostearate, diisopropanolamine isostearate, and diisopropanolamine myristate.

14. The patch preparation according to claim 1, wherein said lipophilic mass base comprises styrene-isoprene-styrene block copolymer.

15. The patch preparation according to claim 1, wherein said drug is selected from a small molecular medicinal compound, a protein medicine, an antigen peptide, or a nucleic acid derivative.

16. The patch preparation according to claim 1, wherein the ionic liquid consists of one or more alkanolamine organic carboxylates.

17. The patch preparation according to claim 1, wherein the lipophilic mass base comprises an elastomer, a tackifier, and a softening agent.

18. The patch preparation according to claim 17, wherein the elastomer comprises one or more rubbers selected from the group consisting of synthetic rubbers, acrylic acid resins, and natural rubbers.

19. The patch preparation according to claim 18, wherein the synthetic rubber is selected from the group consisting of styrene-isoprene-styrene copolymer (SIS), silicon rubbers, polystyrene-butadiene copolymer, and polyisobutylene.

20. The patch preparation according to claim 17, wherein the tackifier is selected from the group consisting of a SIS resin, a polyterpene resin, a polyolefin resin, a polystyrene resin, an aromatic petroleum resin, rosin, and hydrogenated rosin.

21. The patch preparation according to claim 17, wherein the softening agent is selected from the group consisting of petroleum-based softening agents; fatty oil-based softening agents; purified lanolin; and liquid paraffin.

* * * * *

UNITED STATES PATENT AND TRADEMARK OFFICE
CERTIFICATE OF CORRECTION

PATENT NO.       : 10,543,275 B2
APPLICATION NO.  : 14/408649
DATED            : January 28, 2020
INVENTOR(S)      : Hidetoshi Hamamoto et al.

It is certified that error appears in the above-identified patent and that said Letters Patent is hereby corrected as shown below:

In the Claims

Column 19, Lines 63-64 In Claim 1, "dissolved in an ionic liquid" should be changed to --dissolved in an organic solvent that comprises an ionic liquid--, and Lines 66-77, "both in the ionic liquid and in the lipophilic mass base" should be changed to --both in the organic solvent and in the lipophilic mass base--.

Column 20, Lines 7-8 In Claim 2, "dissolved in an ionic liquid" should be changed to --dissolved in an organic solvent that comprises an ionic liquid--, and Lines 11-12, "both in the ionic liquid and in the lipophilic mass base" should be changed to --both in the organic solvent and in the lipophilic mass base--.

Column 20, Lines 16-17 In Claim 3, "dissolved in an ionic liquid" should be changed to --dissolved in an organic solvent that comprises an ionic liquid--, and Lines 19-20, "both in the ionic liquid and in the lipophilic mass base" should be changed to --both in the organic solvent and in the lipophilic mass base--.

Signed and Sealed this
Thirty-first Day of March, 2020

Andrei Iancu
*Director of the United States Patent and Trademark Office*